(12) United States Patent
Holland

(10) Patent No.: US 11,259,553 B2
(45) Date of Patent: *Mar. 1, 2022

(54) DIETARY SUPPLEMENTATION WITH MIXED ALKALI SALTS

(71) Applicant: Ryan Holland, Trent Woods, NC (US)

(72) Inventor: Ryan Holland, Trent Woods, NC (US)

(73) Assignee: LitholLyte Corporation, LLC, New Bern, NC (US)

( * ) Notice: Subject to any disclaimer, the term of this patent is extended or adjusted under 35 U.S.C. 154(b) by 49 days.

This patent is subject to a terminal disclaimer.

(21) Appl. No.: 16/794,988

(22) Filed: Feb. 19, 2020

(65) Prior Publication Data

US 2020/0178588 A1    Jun. 11, 2020

Related U.S. Application Data

(63) Continuation-in-part of application No. 16/108,886, filed on Aug. 22, 2018, now Pat. No. 10,986,857.

(60) Provisional application No. 62/548,905, filed on Aug. 22, 2017.

(51) Int. Cl.
| | |
|---|---|
| *A23L 33/125* | (2016.01) |
| *A23L 33/16* | (2016.01) |
| *A23L 33/17* | (2016.01) |
| *A23L 33/15* | (2016.01) |
| *A61K 9/00* | (2006.01) |
| *A61K 9/20* | (2006.01) |
| *A61K 31/047* | (2006.01) |
| *A61K 31/191* | (2006.01) |
| *A61P 13/12* | (2006.01) |
| *A61K 9/14* | (2006.01) |

(52) U.S. Cl.
CPC ............. *A23L 33/16* (2016.08); *A23L 33/125* (2016.08); *A23L 33/15* (2016.08); *A23L 33/17* (2016.08); *A61K 9/0053* (2013.01); *A61K 9/0095* (2013.01); *A61K 9/14* (2013.01); *A61K 9/20* (2013.01); *A61K 31/047* (2013.01); *A61K 31/191* (2013.01); *A61P 13/12* (2018.01)

(58) Field of Classification Search
CPC ........ A23L 33/16; A23L 33/17; A23L 33/125; A23L 33/15; A61K 9/20; A61P 13/12
See application file for complete search history.

(56) References Cited

U.S. PATENT DOCUMENTS

| | | | |
|---|---|---|---|
| 4,888,182 A | 12/1989 | Pak | |
| 6,610,206 B1* | 8/2003 | Callan | A61K 31/19 |
| | | | 210/646 |
| 9,278,112 B2 | 3/2016 | Goldfarb et al. | |
| 9,737,564 B2 | 8/2017 | Goldfarb et al. | |
| 9,895,396 B2 | 2/2018 | Goldfarb et al. | |
| 2004/0082502 A1 | 4/2004 | Gans | |
| 2009/0053389 A1* | 2/2009 | Vangala | A23L 2/52 |
| | | | 426/658 |
| 2010/0167990 A1 | 7/2010 | Poulsen | A61K 9/0019 |
| | | | 514/4.8 |
| 2013/0200101 A1 | 8/2013 | Dooley | A47J 31/404 |
| | | | 222/129.4 |
| 2014/0271929 A1 | 9/2014 | Goldfarb et al. | |
| 2015/0366906 A1 | 12/2015 | Schmotter | A23L 2/52 |
| | | | 424/601 |
| 2016/0184349 A1 | 6/2016 | Goldfarb et al. | |
| 2017/0340664 A1 | 11/2017 | Goldfarb et al. | |
| 2018/0169144 A1 | 6/2018 | Goldfarb et al. | |
| 2019/0059432 A1* | 2/2019 | Holland | A61K 31/194 |

FOREIGN PATENT DOCUMENTS

| | | | |
|---|---|---|---|
| CN | 103098890 | | 5/2013 |
| WO | WO 2007/035760 | * | 3/2007 |

OTHER PUBLICATIONS

PubChem, Magnesium citrate (Jun. 27, 2020), pp. 1-50 (Year: 2020).*
Sugar and Sweetener Guide, Erythritol, (Mar. 26, 2019), pp. 1-3 (Year: 2019).
Zerwekh, Joseph et al., The Journal of Urology, vol. 177 (Jun. 2007), pp. 2179-2184 (Year: 2007).
PubChem, Sodium bicarbonate, accessed Mar. 25, 2019, pp. 1-3 (Year: 2019).
Endmemo, Magnesium citrate, acessed Mar. 25, 2019, pp. 1-2 (Year: 2019).
Eisner et al. J Urol. Jun. 2010;183(6):2419-23. Citrate, malate and aikali content in commonly consumed diet sodas: implications for nephrolithiasis treatment.
Ettinger, et al. J Urol. Dec. 1997;158(6):2069-73. Potassium-magnesium citrate is an effective prophylaxis against recurrent calcium oxalate nephrolithiasis.
Kang, et al. J Urol. Apr. 2007;177:1358-1362. Long-Term Lemonade Based Dietary Manipulation in Patients with Hypocitraturic Nephrolithiasis.

(Continued)

*Primary Examiner* — Andrew S Rosenthal
*Assistant Examiner* — Lyndsey M Beckhardt
(74) *Attorney, Agent, or Firm* — Stanek Lemon Crouse & Meeks, PA

(57) ABSTRACT

The present invention provides compositions and methods for the dietary management of nephrolithiasis and hypocitraturia through the oral administration of multiple alkali salts including sodium bicarbonate, potassium citrate and/or magnesium citrate. Also provided are kits including compositions for the dietary management of nephrolithiasis and hypocitraturia.

10 Claims, No Drawings

(56) References Cited

OTHER PUBLICATIONS

Odvina, et al. Clin J Am Soc Nephrol. Nov. 2006;1(6):1269-74. Comparative value of orange juice versus lemonade in reducing stone-forming risk.
Pinheiro, et al. Urology. Jul. 2013;82(1):33-7. doi: 10.1016/j.urology.2013.03.002.The effect of sodium bicarbonate upon urinary citrate excretion in calcium stone formers.
Preminger, et al. J Urol. Feb. 1988;139(2):240-2. Alkali action on the urinary crystallization of calcium salts: contrasting responses to sodium citrate and potassium citrate.
Riley, et al. J Endourol. Dec. 1, 2013; 27(12): 1487-1492. Effect of Magnesium on Calcium and Oxalate Ion Binding.
Shipman, Matt, "The Difference Between Baking Soda and Baking Powder," May 21, 2014. pp. 1-4.
Schmiedl, A., et al., "Reappraisal of the Quantity and Nature of Renal Calcifications and Mineral Metabolism Magnesium-Deficient Rat," Urol Int 61, 1998. pp. 76-85.

* cited by examiner

DIETARY SUPPLEMENTATION WITH MIXED ALKALI SALTS

RELATED APPLICATION DATA

This application is a continuation-in-part application of U.S. patent application Ser. No. 16/108,886, filed Aug. 22, 2018, which claims priority from and the benefit of U.S. Provisional Application Ser. No. 62/548,905, filed Aug. 22, 2017. The disclosures of which are incorporated herein by reference in their entireties.

FIELD

The present invention relates to compositions and methods of dietary supplementation, and more particularly, to compositions and methods for the dietary management of kidney disorders, such as nephrolithiasis, through the oral administration of multiple alkali salts.

BACKGROUND

Nephrolithiasis is a common disease, with an estimated lifetime risk in the western world of 10-20%. Following proper treatment even first time kidney stone formers have a risk of recurrence that is increased with each subsequent kidney stone. Up to 60% of kidney stone formers are at risk due to a deficiency of urinary citrate, termed hypocitraturia. That is, hypocitraturia is a common metabolic deficiency found in patients with recurrent nephrolithiasis.

Potassium citrate is commonly used as first line therapy for the management of hypocitraturia, however, patient compliance may be difficult due to gastrointestinal disturbances and/or medication expense. In addition, some patients simply prefer nonprescription therapy.

Although patients may be capable of dietary modification as opposed to ingesting prescription pills for the prevention of nephrolithiasis, the known dietary measures for doing so remain arduous. Kang, et al. (Journal of Urology 2007; April 177(4):1358-62) report that two liters of lemonade from concentrate per day sustained increases in urinary citrate equal to that of 40 mEq potassium citrate tablets per day. To date there are a paucity of readily available dietary measures that are designed to increase urinary citrate for kidney stone prevention.

It is known that the overall prevalence of chronic kidney disease (renal failure) in the general population is approximately 14 percent. It is also known that those with chronic kidney disease have impaired renal clearance of potassium and therefore are at risk for dangerously high blood levels of potassium, termed hyperkalemia. Moreover, it is known that a history of kidney stones is a risk factor for chronic kidney disease formation. To date there are no ultra-low potassium dietary measures available that are designed to increase urinary citrate for kidney stone prevention.

SUMMARY

According to the present invention, compositions and methods are disclosed that may significantly and unexpectedly improve the dietary management of kidney disorders, such as nephrolithiasis, through the oral administration of a composition including alkali salts. In particular embodiments, the alkali salts are potassium, sodium, and magnesium alkaline salts. In some embodiments, the salts are sodium bicarbonate, tripotassium citrate monohydrate and trimagnesium dicitrate.

In some embodiments, the present invention relates to a dietary supplement including sodium bicarbonate, potassium citrate and magnesium citrate. In particular aspects, the supplement may further include a sugar alcohol.

In other embodiments, the composition or supplement is a beverage, tablet, or powdered mixture, and in further embodiments, a beverage enhancer, and in some embodiments, a ready-to-mix or ready-to-drink beverage.

In still other embodiments, the present invention provides a composition including alkali salts, such as sodium bicarbonate, potassium citrate and magnesium citrate, a sugar alcohol and water.

In particular embodiments, the compositions or supplements relate to a low or ultra-low potassium composition.

Embodiments of the present invention further provide methods of reducing kidney stone formation or managing hypocitraturia in a subject including providing to the subject a composition or supplement including alkali salts, such as sodium bicarbonate, potassium citrate and magnesium citrate, and optionally including a sugar alcohol. In particular embodiments, the methods impart a low or ultra-low potassium method of kidney health management where the composition or supplement of the present invention may be a low or ultra-low potassium composition or supplement.

Still further embodiments of the present invention provide a kit including at least one container including a composition including a powdered mixture, beverage or tablet including alkali salts, such as sodium bicarbonate, potassium citrate and magnesium citrate, and optionally including a sugar alcohol, and instructions for use thereof. In some embodiments, the container is adapted for dispensing a predetermined measured amount of the composition for the treatment or prevention of kidney stones or management of hypocitraturia.

DETAILED DESCRIPTION

The present invention is further described below in greater detail with accompanying examples. The embodiments and advantages of the present invention may be attained by means of the elements and combinations thereof as described herein. It is to be understood that both the foregoing general description and the following detailed description are exemplary and explanatory and support the invention as claimed. Hence, the following specification is intended to illustrate some particular embodiments of the invention, and not to exhaustively specify all permutations, combinations and variations thereof.

As used herein, "a," "an" or "the" can mean one or more than one. Also as used herein, "and/or" refers to and encompasses any and all possible combinations of one or more of the associated listed items, as well as the lack of combinations when interpreted in the alternative ("or").

The term "about," as used herein when referring to a measurable value is meant to encompass variations of +/−20%, +/−10%, +/−5%, +/−1%, +/−0.5%, or even +/−0.1% of the specified amount.

As used herein, "alkali salts" include sodium citrate, sodium bicarbonate, potassium citrate, potassium bicarbonate, and magnesium citrate, magnesium bicarbonate, and salts of malic acid.

As used herein, "kidney disorders" include, but are not limited to, hyperoxaluria; hypocitraturia, hyperuricosuria; urolithiasis, including nephrolithiasis, ureterolithiasis and cystolithiasis; accumulation of calcium crystals; obstruction in urine output; creatinine clearance and recurrence of stone formation.

As used herein, "supplement" is a composition not limited to a specific formulation. For example, a supplement may be prepared in various formulations such as a pill, granule, tablet, powder, capsule, or beverage formulation. These formulations may be easy to carry and take anywhere, anytime and used in addition to a subject's normal dietary intake in order to provide additional benefits. In some instances, the supplement is added to a food product or beverage. It should be noted that the terms beverage and drink are used interchangeably.

"Treat," "treating" or "treatment" as used herein refers to any type of action or administration that imparts a benefit to a subject that has a disease or disorder, including improvement in the condition of the subject (e.g., reduction or amelioration of one or more symptoms), healing, etc.

The term "prevent," "preventing" or "prevention of" (and grammatical variations thereof) refers to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression are less than what would occur in the absence of carrying out the steps of the methods of the present invention.

A "therapeutically effective amount," "treatment effective amount" and "effective amount" as used herein are synonymous unless otherwise indicated, and mean an amount of a composition or formulation of the present invention that is sufficient to improve the condition, disease, or disorder being treated and/or achieved the desired benefit or goals as described herein. Those skilled in the art will appreciate that the therapeutic effects need not be complete or curative, as long as some benefit is provided to the subject. Similarly, a "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

"Subject" as used herein refers to any subject in whom prevention and/or treatment of a kidney disorder is needed or desired, as well as any subject prone to a kidney disorder or any subject desirous of maintaining kidney health and/or function. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., for veterinary medicine or pharmaceutical drug development purposes or animal healthcare purposes.

The subjects may be male or female and may be of any race or ethnicity, including, but not limited to, Caucasian, African-American, African, Asian, Hispanic, Indian, etc. and combinations thereof. The subjects may be of any age, including newborn, neonate, infant, child, adolescent, adult, and geriatric. In some embodiments, the subject has been diagnosed with a kidney disorder, is at risk for developing a kidney disorder, or for whom it is generally desirable to prevent a kidney disorder. In some embodiments, the subject is a diabetic or pre-diabetic subject.

Embodiments of the present invention provide compositions that include multiple alkali salts in amounts that deliver alkali to individuals such that the incidence of kidney disorders, such as nephrolithiasis, is reduced. The compositions include multiple urinary citrate-increasing components, generally mixed alkali salts. In general, consumption of the composition raises urinary citrate levels. Thus, subjects experience improved dietary management of various kidney disorders.

According to embodiments of the present invention, the present invention provides a supplement comprising, consisting essentially of, or consisting of alkali salts such as sodium citrate, sodium bicarbonate, potassium citrate, tripotassium citrate monohydrate, potassium bicarbonate, magnesium citrate, tripotassium citrate monohydrate, magnesium bicarbonate, calcium citrate, tricalcium dicitrate and salts of malic acid. In particular embodiments, the salts are sodium bicarbonate, tripotassium citrate monohydrate and trimagnesium dicitrate.

In some embodiments, the supplement may also include a sugar alcohol. The sugar alcohol may be sorbitol, mannitol, xylitol, maltitol, maltitol syrup, lactitol, erythritol, isomalt, sucralose, maltodextrin, hydrogenated starch hydrolysates and combinations thereof. In particular embodiments, the sugar alcohol is erythritol.

In some embodiments, the composition may also include citric acid. Yet in other embodiments, the supplement does not include citric acid as a component of the composition thereof or as an additive provided in combination with the supplement.

In further embodiments, the supplement contains 40 or fewer calories, i.e., any integer including and in between zero to 40 and includes all ranges therebetween and is a "low calorie" supplement. In particular embodiments, the supplement contains less than 10 calories. In some embodiments, the supplement contains less than five calories and is considered "calorie free." In still other embodiments, the supplement contains zero calories.

In some embodiments, the supplement is tasteless. That is, subjects are unable to detect the presence and/or flavor of the formulation when mixed in water or with other beverages. The amounts of the salts and/or sugar alcohols in the compositions of the present invention is below the taste threshold. The tastelessness of the supplement provides an improved palatability compared to the taste of conventional alkali salt containing supplements and compositions used in the management of kidney disorders.

In still other embodiments, the pH of the supplement is from 3.3 to 8.0, that is, the pH value upon mixing the ingredients is generally from 3.3 to 8.0 and all values to the tenth decimal place therebetween and includes all ranges therebetween. In some embodiments, the pH is 6.8 to 8.0. In some embodiments, the pH is 7.0.

According to additional embodiments of the present invention, the supplement is a beverage, tablet, or powdered mixture (or "mix"). The supplement may be a concentrated liquid (concentrate). In some embodiments, the powdered mix, concentrated liquid or a tablet, which upon mixing with a suitable liquid (such as water) or diluting (if it is concentrate), will provide a beverage of the present invention. In some embodiments, the beverage is a clear or translucent beverage.

The beverage can be packaged in suitable containers such as bottles, cans, cardboard packages, squeeze pouches or packets, etc. in any suitable size including up to 0.5, 1, 1.5 or 2 liter portions. The beverages can be aseptically packaged and stored at ambient temperatures or at refrigeration temperatures. In particular embodiments, the beverage can be tasteless, clear, translucent, low calorie and/or zero calorie.

In some embodiments, the supplement or composition is a ready to drink beverage or a concentrated beverage that can be diluted and ready to drink.

The powdered mix, concentrate and the tablets can be packaged in suitable containments—such as paper or foil packages or pouches (such as stick packs) for the powdered mix, cartons, bottles, containers, or boxes for the concentrate, and blister packages for tablets. The powdered mix, concentrate or the tablet can be portioned such that they can be made into a preselected volume of beverage. For example, the powdered mix, concentrate or the tablet can be portioned such that it makes up 0.5 liter, half liter, liter and a half, or a liter of beverage. The supplement or composition can be packaged as single-cup coffee or tea packages.

A multitude of flavors and/or colors can be added to the supplement or composition as desired. In one embodiment, the color, flavor or other additive does not add any caloric value to the product. Flavors may be natural or artificial. Examples of suitable flavors include, but are not limited to, orange, grape, apple, pineapple, mango, papaya, guava, lychee, watermelon, cherry, lemon, lime, fruit punch, pomegranate, grapefruit, strawberry, cranberry, blueberry, blackberry, raspberry, acai berry, cranberry, elderberry, mulberry, lingonberry, boysenberry, dragon fruit, ginger, coffee, tea, chocolate, vanilla, caramel, etc. and combinations thereof.

Embodiments of the present invention provide beverage enhancers that are added to beverages such as water, coffee, tea, juice, sports drinks, etc. after production of the beverage, or the compositions may be formulated as a component of the water, coffee, tea, juice, sports drinks, etc. beverage product to provide the final manufactured beverage product that includes the compositions of the present invention.

Further embodiments of the present invention provide a composition comprising, consisting essentially of or consisting an alkali salt, such as sodium bicarbonate, potassium citrate, and magnesium citrate, and a sugar alcohol as described above, and water, or in particular embodiments, sodium bicarbonate, tripotassium citrate monohydrate and trimagnesium dicitrate, and a sugar alcohol as described above, and water.

In particular embodiments, the composition includes citric acid as a component thereof or as an additive provided in combination with the composition. Citric acid is a GRAS food additive that is well absorbed and is excreted into the renal tubule where it forms soluble complexes with calcium, reducing the concentration of free calcium in the urine. Citric acid can be in the form of citric acid or a citrate salt such as magnesium citrate, calcium citrate or other physiologically acceptable salts.

In other embodiments, the composition does not include citric acid as a component thereof or as an additive provided in combination with the composition.

According to embodiments of the present invention, the composition contains 40 or fewer calories, i.e., any integer including and in between zero to 40 and includes all ranges therebetween and is a "low calorie" supplement. In particular embodiments, the composition contains less than 10 calories. In some embodiments, the composition contains less than five calories and is considered "calorie free." In still other embodiments, the composition contains zero calories.

In some embodiments, the composition is tasteless. In still other embodiments, the pH of the composition is from is 3.3 to 8.0 with all values and ranges therebetween. In some embodiments, the pH is 6.8 to 7.2. In still some embodiments, the pH is 7.0.

In some other embodiments, the composition further includes vitamins, minerals, amino acids, or a combination thereof. Exemplary vitamins include vitamin B1, vitamin B2, niacinamide, vitamin B12, folic acid, vitamin C, and vitamin E. Exemplary minerals include iron, zinc, vanadium, selenium, chromium, boron, potassium, manganese, copper and magnesium. Exemplary amino acids include lysine, isoleucine, leucine, threonine, valine, tryptophan, phenylalanine, methionine and L-selenomethionine.

In particular embodiments, the composition comprises, consists essentially of, or consists of about 1 to 10 mmol/L sodium bicarbonate, about 0.8 to 3 mmol/L potassium citrate, about 0.6 to 2.5 mmol/L magnesium citrate, and about 400 to 800 mg/L erythritol, wherein the pH of the composition is 3.3-8.0. In still further embodiments, the composition comprises, consists essentially of, or consists of about 7 mmol/L sodium bicarbonate, about 2.65 mmol/L potassium citrate, about 0.82 mmol/L magnesium citrate; about 700 mg/L erythritol, wherein the pH of the composition is 7.0.

Embodiments of the present invention also provide a ready to drink formulation. The ready to drink beverage may be low calorie, calorie free or contain zero calories. One half to 2 liters of the liquid can be consumed over an entire day to increase urinary citrate levels. This ready to drink form is useful for the subjects described above, such as those individuals who have been diagnosed with hypocitraturia and for individuals who are at risk for developing nephrolithiasis.

In another embodiment, the present invention provides a tablet or powder form that when combined with liquid which is organoleptically acceptable to humans, and 1 liter provides 1 to 10 mmol of sodium bicarbonate; 0.8 to 3 mmol of potassium citrate; 0.6 to 2.5 mmol of magnesium citrate; and 400 to 1600 mg erythritol. Inactive substances such as flavoring and coloring may be added to the liquid. The resulting beverage may be low calorie, calorie free or contain zero calories.

In particular embodiments, the composition whether in the form of a supplement, beverage, powdered mixture, tablet, etc. contains ultra-low levels of potassium (derived from potassium citrate), with potassium citrate ranging 0.8 to 3 mmol/L potassium citrate and therefore elemental potassium 0.28 mmol/L to 0.6 mmol/L.

In still other embodiments, the present invention provides a zero calorie supplement comprising, consisting essentially of, or consisting of multiple urinary citrate increasing components.

The present invention also provides a method for reducing the incidence of nephrolithiasis. The method includes providing to an individual a supplement of the present invention in an amount that is sufficient to reduce the incidence of kidney stones. It is considered that the present supplement alters urine composition to make the urine less opportune for nephrolithiasis formation, by raising urinary citrate.

The present invention further provides a method for reducing the incidence of nephrolithiasis in patients afflicted with chronic kidney disease. It is considered that the present ultra-low potassium supplement alters urine composition to make the urine less opportune for nephrolithiasis formation, by raising urinary citrate.

Accordingly, embodiments of the present invention provide a method of reducing kidney stone formation or managing hypocitraturia in a subject comprising, consisting essentially of, or consisting of providing to the subject a composition comprising, consisting essentially of, or consisting of sodium bicarbonate, potassium citrate and magnesium citrate. In some embodiments, the composition further includes a sugar alcohol as described above.

In particular embodiments, the method provides ultra-low levels of potassium.

In some embodiments, the subject has chronic kidney disease. In some embodiments, the subject has experienced recurrent nephrolithiasis. In still other embodiments, the subject has hypocitraturia. The hypocitraturia may be severe hypocitraturia characterized by citrate excretion of less than 100 mg per day, or mild to moderate hypocitraturia characterized by citrate excretion of 100-320 mg per day. In some embodiments of the present invention, the subject is a diabetic or pre-diabetic subject.

Embodiments of the present invention also include a method for increasing urinary citrate by providing a supplement to an individual, said supplement essentially consisting of 1 to 10 mmol/L sodium bicarbonate; 0.8 to 3 mmol/L potassium citrate; 0.6 to 2.5 mmol/L magnesium citrate; and 400 to 1600 mg/L erythritol, wherein the pH of the beverage is 3.3-8.0.

Embodiments of the present invention further include a method for reducing the incidence of nephrolithiasis in patients stricken with chronic kidney disease, said supplement essentially consisting of 1 to 10 mmol/L sodium bicarbonate; 0.8 to 3 mmol/L potassium citrate; 0.6 to 2.5 mmol/L magnesium citrate; and 400 to 1600 mg/L erythritol, wherein the pH of the beverage is 3.3-8.0.

Additionally, embodiments of the present invention provide a method for dietary management of kidney stone disease in humans including administration of a supplement including multiple urinary citrate increasing components.

Further embodiments include a method for reducing the incidence of nephrolithiasis in subjects afflicted with chronic kidney disease, including administration of a supplement including multiple urinary citrate increasing components and ultra-low levels of potassium as defined prior.

Still further embodiments include a method for increasing urinary citrate by providing a supplement to an individual, said supplement consisting of 1 to 10 mmol/L sodium bicarbonate; 0.8 to 3 mmol/L potassium citrate; 0.6 to 2.5 mmol/L magnesium citrate; and 400 to 1600 mg/L erythritol, wherein the pH of the supplement is 3.3-8.0.

Embodiments of the present invention also include a method for increasing urinary citrate by providing a supplement to an individual, said supplement including 7 mmol/L sodium bicarbonate; 2.65 mmol/L potassium citrate; 0.82 mmol/L magnesium citrate; and 700 mg/L erythritol, wherein the pH of the supplement is 7.0.

Embodiments further include a method for dietary management of kidney stones in a human in need thereof including administering a supplement to the human, said supplement including 1 to 10 mmol/L sodium bicarbonate; 0.8 to 3 mmol/L potassium citrate; 0.6 to 2.5 mmol/L magnesium citrate; and 400 to 1600 mg/L erythritol, wherein the pH of the supplement is 3.3-8.0.

Still other embodiments provide a method for dietary management of kidney stones in a human in need thereof including administering a supplement to the human, said supplement including 7 mmol/L sodium bicarbonate; 2.65 mmol/L potassium citrate; 0.82 mmol/L magnesium citrate; and 700 mg/L erythritol, wherein the pH of the supplement is 7.0.

Further embodiments include a method for reducing the incidence of nephrolithiasis in subjects afflicted with chronic kidney disease, said supplement essentially consisting of 1 to 10 mmol/L sodium bicarbonate; 0.8 to 3 mmol/L potassium citrate; 0.6 to 2.5 mmol/L magnesium citrate; and 400 to 1600 mg/L erythritol, wherein the pH of the supplement is 3.3-8.0.

Still further embodiments provide a method for reducing the incidence of nephrolithiasis in subjects afflicted with chronic kidney disease, said supplement essentially consisting of 7 mmol/L sodium bicarbonate; 2.65 mmol/L potassium citrate; 0.82 mmol/L magnesium citrate; and 700 mg/L erythritol, wherein the pH of the supplement is 7.0.

Embodiments of the present invention also provide kits including an assembly of components described herein. In particular, the kits comprise, consist essentially of or consists of at least one container comprising a composition comprising a powdered mixture, beverage or tablet comprising, consisting essentially of or consisting of an alkali salt, such as, sodium bicarbonate, potassium citrate and magnesium citrate, and optionally a sugar alcohol, such as erythritol; and instructions for use thereof. In some embodiments, composition includes sodium bicarbonate, tripotassium citrate monohydrate and trimagnesium dicitrate, and optionally citrate and/or a sugar alcohol.

In further embodiments, the present invention provides a kit including a powdered mix, concentrated liquid or a tablet, which upon mixing with a suitable liquid (such as water) or diluting (if it is concentrate), will provide the beverage of the present invention. The kit may also contain a set of instructions for preparing the beverage from the powdered mix, concentrate or the tablet and for consumption. The set of instructions may provide the frequency and the amount of beverage to be consumed over a 24 hour (or other selected) period. The set of instructions may also provide storage recommendations.

Further, the packaging of the products according to embodiments of the present invention can be in suitable portions allowing packing together of the supply for a day, week, month, etc. and may include instructions regarding consumption of the same and/or storage recommendations.

Embodiments of the present invention provide provides a kit including beverage enhancers that are added to beverages such as water, coffee, tea, juice, sports drinks, etc. after production of the beverage, or the compositions may be formulated as a component of the water, coffee, tea, juice, sports drinks, etc. beverage product to provide the final manufactured beverage product that includes the compositions of the present invention.

In particular embodiments, the container housed in the kit is adapted for dispensing a predetermined measured amount of the composition for the treatment or prevention of kidney stones or management of hypocitraturia.

EXAMPLES

Some aspects of the present invention are described in more detail in the following non-limiting Examples. These are not intended to restrict the present invention, and may be modified within the range not deviating from the scope of this invention.

Supplement 1
 1 to 10 mmol/L sodium bicarbonate;
 0.8 to 3 mmol/L potassium citrate;
 0.6 to 2.5 mmol/L magnesium citrate; and
 400 to 1600 mg/L erythritol
 wherein the pH of the supplement is 3.3-8.0.

Supplement 2
  7 mmol/L sodium bicarbonate;
  2.65 mmol/L potassium citrate;
  0.82 mmol/L magnesium citrate; and
  700 mg/L erythritol
  wherein the pH of the supplement is 7.0.
Supplement 3
  1 to 10 mmol/L sodium bicarbonate;
  0.8 to 3 mmol/L potassium citrate;
  0.6 to 2.5 mmol/L magnesium citrate; and
  400 to 1600 mg/L erythritol,
  wherein the pH of the beverage is 3.3-8.0 and wherein the supplement contains zero calories.
Supplement 4
  7 mmol/L sodium bicarbonate;
  2.65 mmol/L potassium citrate;
  0.82 mmol/L magnesium citrate; and
  700 mg/L erythritol,
  wherein the pH of the beverage is 7.0 and wherein the supplement contains zero calories.
Powdered Mix 1
  A powdered mix or a tablet including: sodium bicarbonate, potassium citrate, magnesium citrate, and erythritol in amounts such that a beverage prepared using the powdered mix will result in 1 to 10 mmol/L sodium bicarbonate; 0.8 to 3 mmol/L potassium citrate; 0.6 to 2.5 mmol/L magnesium citrate; and 400 to 1600 mg/L erythritol, wherein the pH of the beverage is 3.3-8.0.
Powdered Mix 2
  A powdered mix or a tablet including: sodium bicarbonate, potassium citrate, citric acid, magnesium citrate, and erythritol in amounts such that a beverage prepared using the powdered mix will have 7 mmol/L sodium bicarbonate; 2.65 mmol/L potassium citrate; 0.82 mmol/L magnesium citrate; and 700 mg/L erythritol, wherein the pH of the beverage is 7.0.
Powdered Mix 3—Litholyte®
  A citrate and bicarbonate based powdered mix water enhancer for kidney health including potassium citrate, sodium bicarbonate, magnesium citrate and erythritol.
  about 7 mmol/L sodium bicarbonate;
  about 2.65 mmol/L potassium citrate;
  about 0.82 mmol/L magnesium citrate; and
  about 700 mg/L erythritol,
  wherein the pH of the composition is 7.0.
  One to two stick packs are mixed with 16.9 oz (500 ml) bottle of water. The resulting product has zero calories, no taste, and no artificial preservatives.
  The beverage can be taken two times a day, or as otherwise directed by a medical professional.
Powdered Mix 4—Litholyte® (Updated Beverage Enhancer)
  A citrate and bicarbonate based powdered mix beverage enhancer for kidney health including potassium citrate, sodium bicarbonate, magnesium citrate and erythritol.
  1) about 1 to 8 mmol/L sodium bicarbonate;
    about 0.8 to 5 mmol/L tripotassium citrate monohydrate;
    about 0.6 to 2 mmol/L trimagnesium dicitrate; and
    about 400 to 800 mg/L erythritol,
    wherein a pH of the composition is 3.3-8.0.
  2) about 4.8 mmol/L sodium bicarbonate;
    about 3.3 mmol/L tripotassium citrate monohydrate;
    about 0.82 mmol/L trimagnesium dicitrate; and
    about 700 mg/L erythritol,
    wherein the pH of the composition is 7.0.
  The resulting product has zero calories, no added taste, and no artificial preservatives.
  The beverage can be taken two times a day, or as otherwise directed by a medical professional.
Powdered Mix 5—Litholyte® (Coffee Enhancer)
  A citrate and bicarbonate based powdered mix beverage enhancer for kidney health including potassium citrate, sodium bicarbonate, calcium citrate, magnesium citrate and erythritol.
  1) about 1 to 8 mmol/L sodium bicarbonate;
    about 0.8 to 5 mmol/L tripotassium citrate monohydrate;
    about 0.2 to 3 mmol/L tricalcium dicitrate; and
    about 0.6 to 2 mmol/L trimagnesium dicitrate.
  2) about 1.6 mmol/L sodium bicarbonate;
    about 1.6 mmol/L Tripotassium citrate monohydrate;
    about 0.8 mmol/L Tricalcium dicitrate; and
    about 1.5 mmol/L Trimagnesium dicitrate.
Powdered Mix 6—Litholyte® (Juice Enhancer)
  A citrate and citric acid based powdered mix beverage enhancer for kidney health including potassium citrate, magnesium citrate and citric acid.
  1) about 0.8 to 5 mmol/L tripotassium citrate monohydrate;
    about 0.6 to 2 mmol/L trimagnesium dicitrate; and
    about 0.5 to 4 mmol/L citric acid.
  2) about 4.3 mmol/L tripotassium citrate monohydrate;
    about 1.2 mmol/L trimagnesium dicitrate; and
    about 2.6 mmol/L citric acid.
Powdered Mix 7—Litholyte® (Tea Enhancer)
  A citrate and citric acid based powdered mix beverage enhancer for kidney health including potassium citrate, magnesium citrate, calcium citrate and citric acid.
  1) about 0.8 to 5 mmol/L tripotassium citrate monohydrate;
    about 0.6 to 2 mmol/L trimagnesium dicitrate;
    about 0.2 to 3 mmol/L tricalcium dicitrate; and
    about 0.5 to 4 mmol/L citric acid.
  2) about 4 mmol/L tripotassium citrate monohydrate;
    about 1 mmol/L trimagnesium dicitrate;
    about 0.3 mmol/L tricalcium dicitrate; and
    about 0.5 mmol/L citric acid.
Biological Results
Method
  Six subjects with a history of low urinary citrate and nephrolithiasis were selected. Subjects were administered a placebo phase of 1.5 L water for two consecutive days with a 24-hour urine specimen collection on the second day. Subjects then experienced a waiting period of 3-5 days. Subjects then were administered six doses of Powdered mix 3 in three divided doses in 1.5 L water over two consecutive days. On the second day, a repeat 24-hour urine specimen was collected. Palatability was also measured on a scale of 0 to 5 (zero being "tasteless" and five being "extreme taste").
Demographics
  Six subjects completed the trial. Three were male and three were female. The average age was 46. The average weight was 89 kg.
Results
  Statistically significant increases in citrate, pH, urine volume, magnesium and potassium were observed. Average citrate increased by 544 mg/d. Statistically significant decreases in supersaturation of uric acid and supersaturation of calcium oxalate were observed. Data (average values) and statistical significance (when applicable) are provided in the table below.

| Urine | Volume | pH | Calcium | Oxalate | Citrate | SS CaOx | SSCaPh | Palatability |
|---|---|---|---|---|---|---|---|---|
| Baseline | 1.65 | 6.1 | 195 | 35 | 357 | 6.32 | 0.83 | 0 |
| Treatment | 1.97 | 6.7 | 187 | 28 | 901 | 2.89 | 0.93 | 0.33 |
| Statistical Significance | 0.05 | 0.0004 | | | 0.0001 | .0009 | | |

| Urine (Cont'd) | SS UA | UA | Na | K | Mg | Cl | Creatinine | Cr/Kg |
|---|---|---|---|---|---|---|---|---|
| Baseline | 0.69 | 672 | 193 | 51 | 90 | 160 | 1569 | 21 |
| Treatment | 0.35 | 680 | 227 | 118 | 148 | 164 | 1607 | 21.5 |
| Statistical Significance | 0.04 | | | 0.001 | 0.03 | | | |

Urine parameters are expressed as mg/day.
SS = super saturation
CaOx = Calcium Oxalate
Ca = Calcium
Ph = Phosphate
UA = Uric acid
Na = Sodium
K = Potassium
Mg = Magnesium
Cr/Kg = Creatinine/kilogram Discussion The observed statistically significant changes are all effective in reducing the occurrence of nephrolithiasis. It is observed that a formulation of the present invention has a more robust citraturic response than an equivalent dose of potassium citrate alone (400 mg/dl vs 544 mg/d) (Mission Pharmacal. http://www.urocit-k.com/wp-content/uploads/2017/12/Urocit-K.pdf). It is also observed that most subjects were unable to detect the presence or flavor of the formulation when mixed in water which is generally advantageous to patient compliance.

Prophetic Example

It is planned that a larger and more formal version of the experiment be undertaken. A planned thirty patients are being recruited to the experiment. Ten will be labeled non-stone formers, ten will be labeled calcium oxalate stone formers, and ten will be labeled uric acid stone formers. It is planned that the experiment take place with a mix of adult male and female subjects of varying ages and weights.

Subjects will undergo a placebo phase in which they intake 1.5 L of water for three days in a row. On the third day, a 24-hour urine test will be obtained. Following this, a three-day washout phase will occur in which the subjects are allowed to eat and drink as normal. Then, subjects will undergo a treatment phase in which they intake six doses of a formulation of the present invention in three divided doses mixed with 1.5 L water for three days in a row. On the third day, a 24-hour urine test will be obtained.

It is expected that the prophetic example will serve as a statistically higher-powered example of the smaller experiment referenced.

The foregoing is illustrative of the present invention, and is not to be construed as limiting thereof. The invention is defined by the following claims, with equivalents of the claims to be included therein.

That which is claimed is:

1. A composition consisting of:
sodium bicarbonate;
potassium citrate;
magnesium citrate; and
at least one of a sugar alcohol, citric acid or water.

2. The composition of claim 1, wherein the composition is tasteless in water.

3. The composition of claim 1, wherein the composition contains zero calories.

4. The composition of claim 1, wherein the composition is a beverage.

5. The composition of claim 1, wherein the composition is a tablet when the composition consists of sodium bicarbonate, potassium citrate, magnesium citrate and at least one of a sugar alcohol or citric acid.

6. The composition of claim 1 wherein the composition is a powdered mixture when the composition consists of sodium bicarbonate, potassium citrate, magnesium citrate and at least one of a sugar alcohol or citric acid.

7. A method of reducing kidney stone formation or managing hypocitraturia in a subject comprising providing to the subject a composition of claim 1.

8. The method of claim 7, wherein the subject has chronic kidney disease.

9. The method of claim 7, wherein the subject has experienced recurrent nephrolithiasis.

10. The method of claim 7, wherein the subject has hypocitraturia.

* * * * *